(12) United States Patent
Igarashi et al.

(10) Patent No.: US 6,596,766 B1
(45) Date of Patent: Jul. 22, 2003

(54) UTILIZATION OF MATERIAL CONTAINING DOCOSAPENTAENOIC ACID

(75) Inventors: Osamu Igarashi, Sumida-ku (JP); Kengo Akimoto, Mishima-gun (JP); Toshiaki Yaguchi, Ibaraki (JP); Yoshinobu Kiso, Ibaraki (JP)

(73) Assignees: Suntory Limited (JP); Nigase & Company, Ltd. (JP)

( * ) Notice: Subject to any disclaimer, the term of this patent is extended or adjusted under 35 U.S.C. 154(b) by 0 days.

(21) Appl. No.: 09/914,897

(22) PCT Filed: Mar. 6, 2000

(86) PCT No.: PCT/JP00/01355

§ 371 (c)(1),
(2), (4) Date: Jan. 17, 2002

(87) PCT Pub. No.: WO00/51444

PCT Pub. Date: Sep. 8, 2000

(30) Foreign Application Priority Data

Mar. 4, 1999 (JP) ............................................. 11-057769

(51) Int. Cl.[7] ............................................... A61K 31/20
(52) U.S. Cl. ...................... 514/558; 514/560; 554/224; 426/648
(58) Field of Search ................................. 514/558, 560; 426/648; 554/224

(56) References Cited

U.S. PATENT DOCUMENTS 5,444,054 A    8/1995    Garleb et al.

FOREIGN PATENT DOCUMENTS

| JP | 61-204136 | 9/1986 |
| JP | 9-285267 | 11/1997 |
| JP | 10-330781 | 12/1998 |
| WO | WO 9803671 | 1/1998 |

OTHER PUBLICATIONS

Koven, W., et al.; "The Effect of Dietary Arachidonic Acid (20:4n–6) on Growth, Survival and Resistance to Handling Stress in Gilthead Seabream (Sparus Aurata) Larvae"; Database Biosis 'Online!; Biosciences Information Service, Philadelphia, PA, US; 2001; vol. 193, No. 1–2, 2001, pp. 107–122.

Anding, R.H., et al.; "Effects of Dietary Linolenate on the Fatty Acid Composition of Brain Lipids in Rats"; Database Biosis 'Online!; Biosciences Information Service, Philadelphia, PA, U.S.; 1986; vol. 21, No. 11, 1986, pp. 697–701.

Primary Examiner—Deborah D. Carr
(74) Attorney, Agent, or Firm—Fay, Sharpe, Fagan, Minnich & McKee LLP

(57) ABSTRACT

A novel technique for relieving arachidonic acid deficient conditions and maintaining a good fatty acid balance in vivo. Utilizaiton of a DPA-containing material for relieving arachidonic acid deficient conditions and maintaining a good fatty acid balance in vivo; and compositions for relieving arachidonic acid deficient conditions and maintaining a good fatty acid balance in vivo which contain a DPA-containing material in an amount efficacious in relieving arachidonic acid deficient conditions and maintaining a good fatty acid balance in vivo per unit dose.

34 Claims, No Drawings

UTILIZATION OF MATERIAL CONTAINING DOCOSAPENTAENOIC ACID

This application is a 371 of PCT/P00/01355 filed Mar. 6, 2000.

TECHNICAL FIELD

The present invention relates to the use of material containing 4, 7, 10, 13, 16-docosapentaenoic acid (hereinafter, also referred to as "DPA") for relieving arachidonic acid deficient conditions and maintaining a good fatty acid balance in vivo and especially relates to the use of material containing 4, 7, 10, 13, 16-docosapentaenoic acid to prevent the decrease of arachidonic acid levels caused by intake of $\omega 3$ unsaturated fatty acids.

BACKGROUND ART

The two representative families of unsaturated fatty acids are the $\omega 3$ type and $\omega 6$ type. Here, (indicates the number of carbon atoms in a fatty acid, counting from the methyl end to the closest double bond. Recently, the ratio of $\omega 6$ unsaturated fatty acids to $\omega 3$ type fatty acids has been recognized as important.

Various fatty acids including $\omega 6$ type fatty acids, such as linoleic acid, dihomo-γ-linolenic acid, and arachidonic acid, and $\omega 3$ type fatty acids, such as α-linolenic acid, eicosapentaenoic acid, and docosahexaenoic acid, are each known to take on different biological functions. At the same time, and importantly, these two types of unsaturated fatty acids strongly influence each other in their biological functions. In humans, these unsaturated fatty acids cannot be biologically synthesized in vivo, and both types do not inter-convert. Thus, the ratio of $\omega 3$ type to $\omega 6$ unsaturated fatty acids in vivo is expected to reflect the ratio in the source of intake (e.g. food).

Meanwhile, based on a nutrition investigation among the Japanese, the recommended intake ratio of $\omega 6$ unsaturated fatty acids to $\omega 3$ unsaturated fatty acids was approximately 4:1, according to the revised 1994 dietary allowance for the Japanese. (Ministry of Health & Welfare, 5th revised edition, Nihonjin no Eiyo no Shoyoryo (Dietary Allowance for the Japanese), 1994, pp. 56–58.)

In addition, the recent eating habits of the Japanese have been influenced by the diet of Western countries, leading to a marked increase in opportunities to have meals centered on meat, and increase in the intake of $\omega 6$ unsaturated fatty acids in comparison to the $\omega 3$ type. Consequently, the mortality rate due to arteriosclerosis diseases, such as myocardial infarction and cerebral thrombosis is rapidly increasing. To improve this condition, addition of highly concentrated $\omega 3$ unsaturated fatty acids, such as 5, 8, 11, 14, 17-eicosapentaenoic acid (hereinafter, also referred to as "EPA") and 4, 7, 10, 13, 16, 19-docosahexaenoic acid (hereinafter, also referred to as "DHA") to nutrient-supplementing food has been developed.

Eicosanoids (prostaglandin, leukotriene, thromboxane, etc.), each exhibiting different physiological functions, are biosynthesized from EPA in the case of $\omega 3$ unsaturated fatty acids, and from dihomo-γ-linolenic acid and arachidonic acid in the case of $\omega 6$ unsaturated fatty acids. Furthermore, $\omega 3$ type and $\omega 6$ unsaturated fatty acids themselves suppress the fatty acid biosynthetic pathway of another type. For example, EPA intake inhibits the Δ6-desaturase controlling the conversion of linoleic acid, the starting fatty acid in the biosynthesis of $\omega 6$ type fatty acids, to γ-linolenic acid, the chain elongation enzyme controlling the conversion of γ-linolenic acid to dihomo-γ-linolenic acid, and the Δ5-desaturase controlling conversion of dihomo-γ-linolenic acid to arachidonic acid. Consequently, the amount of the final product, arachidonic acid (hereinafter, also referred to as "ARA"), significantly decreases. Intake of ARA-precursor fatty acids (such as, linoleic acid, and γ-linolenic acid) is only slightly effective for supplementing this ARA decrease, and direct intake of ARA was said to be necessary.

Furthermore, in recent years, elucidation of the biologically active functions of DHA and its practical use have progressed due to discovery of fish material that contains high concentrations of DHA, such as the orbital fat of tuna, and technological advancement in producing highly purified fatty acids. It has become apparent that the effect of lowering cholesterol levels, anticoagulant effect, and carcinostatic effect are biologically active functions of DHA. In relation to the metabolic system of the brain, it has also become apparent that DHA is effective in improving memory and learning, preventing senile dementia, and treating Alzheimer's disease. In addition, it has been proven that DHA is an essential fatty acid for the growth of fry. From the above-mentioned reasons, DHA is used in various foods, feedstuffs, and baits. DHA also inhibits the biosynthetic pathway involving $\omega 6$ unsaturated fatty acids, leading to ARA, and this inhibition is known to be stronger than that by EPA. Thus, decline in ARA levels as a secondary effect due to administration of DHA alone is considered a problem.

Administration of DHA alone is hardly a problem if $\omega 3$ unsaturated fatty acids are administered only for a limited period to a particular patient as a medicament, or if administration of DHA supplements lowered levels or complete deficiency of $\omega 3$ unsaturated fatty acids. However, the balance between $\omega 6$ and $\omega 3$ type fatty acids must be considered when $\omega 3$ unsaturated fatty acids are taken to prevent diseases. In the past, direct intake of ARA was necessary to repress the decrease of ARA levels due to intake of $\omega 3$ unsaturated fatty acids. However, controlling the amount of ARA intake is difficult because ARA is the direct precursor of eicosanoids, such as 2-series prostaglandin and 4-series leukotriene.

ARA deficient conditions are not limited to those caused by $\omega 3$ unsaturated fatty acid intake. For example, among infants, the aged, patients with adult diseases, and those at risk of adult diseases such as hepatic diseases, the biosynthetic pathway to produce ARA from linoleic acid is weak, and plainly, ARA In vivo tends to be deficient. Under diseased conditions, prostaglandin and its precursor, ARA, are in high demand for central defense and repair mechanisms in vivo. Therefore, ill patients suffer from deficiency of ARA that may contribute to recovery and survival. Regardless of age, inadequate nutrition leads to ARA deficient conditions. Furthermore, ARA is often deficient in individuals whose fat intake is restricted (for example, due to hyperlipidemia, diabetes, obesity, and so on).

Consequently, techniques to improve ARA deficient conditions and to maintain a good fatty acid balance in vivo, and especially techniques that provide safer alternatives to direct intake of ARA in efforts to prevent decrease of ARA levels caused by intake of $\omega 3$ unsaturated fatty acids were in high demand.

DISCLOSURE OF THE INVENTION

The present invention intends to solve the problems mentioned above and provides a novel technique to improve arachidonic acid deficient conditions and to maintain a good fatty acid balance in vivo, and especially, a novel technique to prevent decrease of arachidonic acid levels caused by intake of $\omega 3$ unsaturated fatty acids.

Upon intensive research to accomplish the objectives described above, the present inventors found that $\omega 6$ type docosapentaenoic acid (4, 7, 10, 13, 16-docosapentaenoic acid, hereinafter, also referred to as "DPA") is converted to arachidonic acid (ARA) in vivo under ARA deficient conditions, and especially under ARA deficient conditions caused by intake of ω3 unsaturated fatty acids. The inventors also found that the resulting increase in ARA levels can affect the fatty acid balance in vivo leading to maintenance of a good fatty acid balance. The present invention was completed based on these findings.

In one embodiment, the present invention provides a use of a DPA containing material for relieving ARA deficient conditions and maintaining a good fatty acid balance in vivo. In another embodiment, the present invention provides a composition for relieving ARA deficient conditions and maintaining a good fatty acid balance in vivo, the composition containing DPA-containing material in an amount efficacious in relieving ARA deficient conditions and maintaining a good fatty acid balance in vivo, per unit dose.

In another embodiment, the present invention provides a method for relieving ARA deficient conditions and maintaining a good fatty acid balance in vivo in mammals excluding humans, the method comprises administering any one of the compositions mentioned above. A method to relieve ARA deficient conditions and maintain a good fatty acid balance in viva in mammals excluding humans is presented.

Application of the present invention to ARA deficient conditions provides significant increase of ARA levels, and allows maintenance of a good fatty acid balance in vivo, for example in the liver and/or serum.

In another embodiment, the present invention provides a use of a DPA-containing material for preventing decrease of ARA levels caused by intake of ω3 unsaturated fatty acids. In a separate embodiment, the present invention provides a composition for preventing decrease of ARA levels caused by intake of ω3 unsaturated fatty acids, the composition containing DPA-containing material in an amount efficacious in relieving decrease of arachidonic acid levels, perunit dose.

In any of the use and compositions mentioned above, the DPA-containing material may be any one or more of DPA-containing lipids selected from a group consisting of lower alkyl esters of DPA and glycerol esters containing DPA as component material. This DPA-containing material may be derived from microorganisms. The microorganisms may be selected from a group consisting of genus Thraustochytriurm, genus Schizochytrium, genus Japonochytriur, and genus Ulkenia.

Any of the compositions mentioned above may be food, food additive, medicament, additive for medicament, feed or bait.

In another embodiment, the present invention provides a method for the production of a composition that prevents the decrease of ARA levels caused by intake of ω3 unsaturated fatty acids, comprising: determining the average amount of intake of ω3 unsaturated fatty acid during a set period by a subject; estimating the decrease of ARA levels in a subject caused by intake of ω3 unsaturated fatty acids; and preparing a unit dose of composition that contains DPA-containing material in an amount efficacious in preventing decrease of ARA levels.

In another embodiment the present invention provides a method for producing a composition that prevents the decrease of ARA levels caused by ω03 unsaturated fatty acid intake, comprising; determining the amount of ω3 unsaturated fatty acids to be included in a composition per unit dose; estimating the decrease of ARA levels in a subject due to intake of ω3 unsaturated fatty acids; and preparing the unit dose composition containing DPA-containing material and ω3 unsaturated fatty acid-containing material in amounts efficacious in preventing decrease of ARA levels.

The DPA-containing material and ω3 unsaturated fatty acid-containing material may be lipids containing DPA and ω3 unsaturated fatty acids. In addition, the total amount of fatty acids in the above-mentioned composition may contain 0.1% or more of DPA; 0.1% or more of DPA and 0.1% or more of 4, 7, 10, 13, 16, 19-docosahexaenoic acid (DHA); and 0.1% or more of DPA, 0.1% or more of DHA, and 20% or less of 5, 8, 11, 14, 17-eicosapentaenoic acid (EPA).

The above-mentioned lipids containing DPA and ω3 unsaturated fatty acids may contain as components, one or more compounds selected from a group consisting of lower alkyl esters of DPA, lower alkyl esters of ω3 unsaturated fatty acids, as well as glycerol esters containing DPA and/or ω3 unsaturated fatty acids.

Especially, the above-mentioned lipids containing DPA and ω03 unsaturated fatty acids may contain as components, either DPA ethyl ester and ω3 unsaturated fatty acid ethyl ester, or triglycerides containing DPA and/or ω3 unsaturated fatty acids.

In another embodiment, the present invention provides lipids containing ARA, DPA, and DHA, where ARA/DHA (weight ratio) is 0.03~0.4, DPA/DHA (weight ratio) is 0.07 or greater, and EPA/DHA (weight ratio) is 0.05 or less. Specifically, DPA/DHA (weight ratio) may be 0.07~5.0.

The above-mentioned lipids may be a mixture of lipids obtained by cultivating one type of microorganism or a mixture of lipids that may be obtained by separately cultivating various microorganisms.

Either of the above-mentioned lipids may contain glycerol esters that include ARA, DPA, and/or DHA as components, specifically it may contain triglycerides that include ARA, DPA, and/or DHA as components.

In another embodiment, this invention provides a nutrient-supplementing food comprising any one of the above-mentioned lipids. This nutrient-supplementing food may be a formula suitable for feeding infants, a formula suitable for feeding premature infants, baby food, food for expectant or nursing mothers, geriatric food, or food for ill patients.

In another embodiment, this invention provides feed for animals comprising any one of the lipids mentioned above.

The possibility that DPA may convert to ARA through retro-conversion has been reported previously (FEBS Letters, 431: 1–6 (1998); Biochim. Biophys. Acta. 137: 420–426 (1967); Biochim. Biophys. Acta. 218: 29–35 (1970); J. Nutrition. 83: 234–238 (1964)). However, these reports only reveal the conversion of DPA to ARA that occurs when DPA is administered to a rat raised on an essential fatty acid-deficient diet such that its ARA levels are excessively decreased in the tissues. Even in administration experiment to normal animals, the report only revealed the conversion of DPA to ARA occurring in the testicles where DPA levels are especially high. The previously reported conversion of DPA to ARA is limited to changes in animals that were raised under special conditions, such as on an essential fatty acid-deficient diet or changes that occurred during a short period within specialized tissues. It was not clarified whether administration of DPA for a long period of time as feed under general nutritional conditions significantly increases the lowered ARA levels in the liver, serum, and such, to maintain a good fatty acid balance. In addition, there had been no indication previously that DPA represses decreased levels of ARA caused by intake of ω3 unsaturated fatty acids.

BEST MODE FOR CARRYING OUT THE INVENTION

The present invention is described in more detail below.

(Utilization of DPA containing material to relieve ARA deficient conditions and maintain a good fatty acid balance in vivo.)

This invention describes the use of DPA-containing material to increase deficient ARA levels in vivo and to maintain a good fatty acid balance. Compositions having this utility comprise DPA-containing material in an amount effective for relieving ARA deficient conditions and maintaining a good fatty acid balance in vivo, per unit dose.

In this description "DPA-containing material" means material containing DPA in any chemical or physical form appropriate for physiological intake of DPA in vivo. Examples of DPA-containing material besides free DPA are inorganic salts of DPA (for example, non-toxic metal salts including alkali metal salts, such as sodium salt and potassium salt; and alkaline earth metal salts, such as calcium salt and magnesium salt), organic salts (for example, ammonium salt), derivatives other than lipids that contain DPA (for example, an amide of DPA and its alkyl substituted forms), and lipids that contain DPA (also simply referred to as "DPA-containing lipids"). DPA-containing lipid is the preferred DPA-containing material in a sense of its physical stability, bio-absorbability and its main constructive form in vivo.

In this description "lipid" refers to a material that is soluble in organic solvents, such as in ether, chloroform, and benzene, but insoluble in water, and has an intramolecular chemical bond, represented by, for example, an ester bond, formed between a higher fatty acid. Examples of DPA-containing lipids are lower alkyl esters of DPA and glycerol esters containing DPA as their components.

In this description "lower alkyl esters of DPA" rid refers to esters formed between DPA and lower alcohols with 1~6 carbons, preferably 1~4 carbons, and more preferably 1~3 carbons. The ethyl ester is especially preferable with regard to bio-acceptability and safety of the alcohol that dissociates upon hydrolysis of the ester bond in vivo. "Glycerol esters containing DPA" or "glycerol esters containing DPA as their component" refers to materials where at least one molecule of DPA forms an ester bond per molecule of glycerol. Such examples include monoacylglyceride, diacylglyceride, triacylglyceride, glycerophospholipid, glyceroglycolipid, etc. Considering application to food, triacylglyceride (also simply called "triglyceride") is preferred from the standpoint of edible forms of fat.

As it is clear to one skilled in the art, DPA-containing lipids are not limited to the examples mentioned above, but also include sphingophospholipids and other phospholipids, sphingoglycolipids and other glycolipids, and any DPA-containing material included in the above definition.

The components per unit dose, and the amount of DPA-containing material included per unit dose for effective relief of ARA deficient conditions and maintenance of a good fatty acid balance in vivo, may be adjusted to suitable levels by one skilled in the art according to the type, sex, age, weight, health condition, or the disease of the subject (humans or other mammals). "Effective for relieving ARA deficient conditions and maintaining a good fatty acid balance in vivo" means that the intake of DPA-containing material causes significant increase of ARA levels, which is enough to restore decreased levels of ARA to normal levels and to maintain a normal level of ARA in vivo. The presence or absence of increase in ARA levels in vivo may be measured by any of the known biochemical methods and/or analytical chemistry methods known to one skilled in the art. As a non-limiting example, in order to relieve ARA deficient conditions and to maintain a good fatty acid balance in vivo in adult humans, compositions containing DPA-containing material for a single administration per day should contain 0.0001 mg~100 g, preferably 0.001 mg~10 g, and more preferably 0.5 mg~5 g of free DPA per unit dose.

Utilization of DPA-containing material of this invention and administration of compositions comprising DPA-containing material may exclude the utilization and administration carried out according to medical prescription by a medical doctor in cases where the patent law applied to applications made by this description includes such limitations. Therefore, practicing the method for relieving ARA deficient conditions and maintaining a good fatty acid balance in vivo, including the process of administering the above-mentioned compositions may be limited to non-human mammals.

(Utilization of DPA-containing Material to Prevent Decrease of ARA Levels)

DPA containing material maybe utilized, especially to prevent decrease of ARA levels caused by the intake of ω3 unsaturated fatty acids. Effective compositions contain DPA-containing material in an amount effective for preventing the decrease of ARA levels caused by the intake of ω3 unsaturated fatty acids, per unit dose. Here "effective for preventing decrease of ARA levels" means sufficient to significantly diminish the magnitude of decrease of ARA levels, or preferably, sufficient to bring ARA to a level that is the same as when ω3 unsaturated fatty acids are not consumed.

The method to produce compositions that prevent the decrease of ARA levels due to ω3 unsaturated fatty acid intake comprises two forms. One is when the source of ω3 unsaturated fatty acid exists separately from this composition, and the other is when the source of ω3 unsaturated fatty acid intake is combined within this composition.

In the former case, first, the average intake of ω3 unsaturated fatty acids during a set period by a subject consuming ω3 unsaturated fatty acids is identified. Based on the identified average intake, the decrease of ARA levels due to the intake of ω3 unsaturated fatty acids by the subject is estimated. In the latter case, first the ω3 unsaturated fatty acid content per unit dose to be included within the composition is identified. This may be determined depending on the primarily intended use of ω3 unsaturated fatty acids (for example DHA and/or EPA). Next, the decrease of ARA levels in a subject caused by intake of a pre-determined amount of ω3 unsaturated fatty acid is estimated. In either case, according to the estimated level of decrease, the amount of DPA effective for preventing decrease of ARA levels is determined. The specific procedures necessary for the process mentioned above may be understood easily by those skilled in the art, and may be carried out appropriately according to the individual subject and the DPA-containing material. Thus, a unit dose of composition comprising an effective amount of DPA-containing material and optionally, ω3 unsaturated fatty acid-containing material can be prepared.

In the above composition, DPA-containing material and ω3 unsaturated fatty acid-containing material are preferably lipids containing DPA and ω3 unsaturated fatty acids. Examples of lipids containing DPA and ω3 unsaturated fatty acids are a mixture of lower alkyl esters of DPA, lower alkyl esters of ω3 unsaturated fatty acids, and glycerol esters containing DPA and/or ω3 unsaturated fatty acids as components. Lipids that contain ω3 unsaturated fatty acids are preferably DHA and/or EPA. In one example, the composition may be characterized by DPA content of not less than 0.1%, preferably not less than 1.0%, or more preferably not less than 3.5% with respect to the total amount of fatty acid within the composition. In another example, the composition may be characterized by a DPA content of not less than 0.1%, preferably not less than 1.0%, and more preferably not less than 3.5% and a DHA content of not less than 0.1%, preferably not less than 1.0%, and more preferably not less than 5.0% with respect to the total amount of fatty acids within the composition. Yet in another example, the composition may be characterized by a DPA content of not less than 0.1%, preferably not less than 1.0%, and more preferably not less than 3.5% and a DHA content of not less than 0.1%, preferably not less than 1.0%, and more preferably not less than 5.0% and an EPA content of not more than 20%, preferably not more than 5.0%, and more preferably not more than 1.0% with respect to the total amount of fatty acids within the composition.

Direct administration of ARA is a simple method to prevent decrease of ARA levels in vivo however, even if the administration takes into account the biologically required amount, that amount varies among individuals and may therefore, in certain cases, cause excessive intake. ARA is the direct precursor of eicosanoids, in contrast, in this invention, the body supplies ARA as necessary, that is, by responding to the decrease of ARA levels, through retroconversion of the administered DPA, and when the ARA level returns to a normal value, retroconversion stops. Normal levels of ARA varies among the tissues however, retroconversion of DPA is regulated to match the normal value in each of the tissues. When the retroconversion of DPA to ARA stops, a surplus of DPA will remain. However, since DPA is not the direct precursor of eicosanoids, and since DPA does not have the effect of increasing ARA to a level that is more than necessary, this will be stocked in vivo as an effective source of ARA, therefore, the effect on the body is indirect and milder than direct administration of ARA.

(Food/medicaments Comprising DPA-containing Material)

Any one of the above-mentioned compositions of this invention is not limited in particular with regard to its mode of use. Representative modes of use include foods, food additives, medicaments, additives for medicaments, feedstuffs, and baits.

Examples of food compositions, besides general foods, are functional foods, nutrient-supplementing foods, formula suitable for feeding infants or premature infants, baby foods, foods for expectant or nursing mothers, and geriatric foods. Examples of foods containing oils and fat include natural foods, which by nature contain oils and fat such as meat, fish, and nut, food to which oils and fat are added upon cooking such as soup, food for which oils and fat are used as heating medium such as doughnuts, oils and fat food such as butter, processed food to which oils and fat are added during processing such as cookies, or food to which oils and fat are sprayed or applied upon completion of processing such as hard biscuits. Furthermore, the lipids of this invention may also be added to agricultural food, fermented food, livestock food, seafood, or drink, which normally do not contain oils and fat. Food additive is a general term for an intermediate product that may be utilized to prepare any of these foods. The definition of food includes functional foods. Functional foods and medicaments may be provided in processed forms such as, enternal agent for promoting nutrition, powder, granule, troche, internal solution, suspension, emulsion, syrup, capsule, and such. Additives for medicaments include intermediate products that may be used to prepare the medicaments of choice. The composition of this invention may also be utilized as feedstuffs for raising animals such as domestic animals, and feed for breeding fish, shellfish, crustacean, and fry.

(Preparation and Purification of DPA-containing Material)

The DPA-containing material of this invention may be obtained from any of the synthetic and natural resources, for example, material that is chemically synthesized and material obtained from plant or animal sources. Examples of plant or animal sources are fish oil, fish powder, fish lees, fish oil extract and so on. Examples of fish oil are oils of sardine, herring, tuna, bonito, saury, menhaden, and such.

Preferably, DPA-containing material may be a DPA-containing lipid derived from microbial cells obtained by cultivating microorganisms that have the ability to produce DPA. DPA-containing lipids derived from microorganisms may be utilized in a variety of forms including the microbial cells themselves, lipid extract extracted from bacterial cells, purified lipids obtained by further purification of the lipid extract, and altered lipids in which the lipid extract or lipid extract are further modified by chemical reactions (for example, esterification).

Microorganisms belonging to any one of the categories shown below are examples of microorganisms that have the ability to produce DPA:

genus Thraustochytrium
genus Schizochytrium
genus Japonochytrium
genus Ulkenia
genus Vibrio
genus Cyclotella
genus Emiliania
genus Isochrysis
genus Nanochloropsis
genus Chaetoceros
genus Phaeodactylum
genus Amphidinium
genus Gonyaulax
genus Peridirmium
genus Chroomonas
genus Cryptomonas
genus Hemiselmis
genus Chiloomonas
genus Chlorella
genus Histiobranchus
genus Coryphenoides
genus Conidiobolus
genus Entomrorhpthora A microorganism belonging to any one of genus Thraustochytrium, genus Schizochytrium, genus Japonochytrium, genus Ulkenia, genus Vibrio, genus Cyclotella, or genus Emiliania is a microorganism that may produce DPA in high proportion with respect to the total amount of fatty acids.

Specific examples of microorganisms mentioned above are the following: bacteria isolated from the deep sea, *Vibrio marinus* ATCC 15381; genus Vibrio bacteria isolated from the intestine of deep sea fish; phlagellate bacteria (such as, *Thraustochytrium aureum* ATCC 34303; Thraustochytrium sp. ATCC 28211, ATCC 20890 and ATCC 20891: Schizochytrium sp. ATCC 20888 and ATCC 20889 (U.S. Pat. No. 5,340,742); genus Thraustochytrium SR21 (Nippon Nogei KagakuKaishi,vol. 69, extra edition, July 5, 1995; National Institute of Bioscience and Human-Technology Agency of Industrial Science Technology accession No. FER MBP-5034); Japonochytriwn sp. ATCC 28207 (Japanese Laid-open(kokai) Patent Publication No. (JP-A) Hei 1-199588 (1989)); microalgae (for example *Cyclotella cryptica*; and Emiliania sp. (JP-A) Hei 5-308976 (1993)). These strains can be obtained, for example, without any restriction from American Type Culture Collection.

SAM2180 strain and SAM2179 strain belonging to the genus Ulkenia, which were isolated from seawater by the present inventors, can also be used favorably as microorganisms that have the ability to produce DPA. The SAM 2179 strain was deposited with the National Institute of Bioscience and Human-Technology, Agency of Industrial Science and Technology (address; 1–3, Higashi 1 chome, Tsukuba-shi, Ibaraki-ken, JAPAN), on Jul. 23, 1996 and assigned an accession No. FERM BP-5601.

Microorganisms capable of producing DPA can be cultivated following standard methods. For example, cultivation can be carried out by inoculating a liquid or solid medium with the microbial strain on a loop, in spores, in mycelium, or as a pre-culture. By cultivation, lipids containing DPA become stored within the microbial cells.

After cultivation, the cultured microbial cells are collected from the culture by conventional solid-liquid separation techniques such as centrifugation and filtration. The cultivated cells are extensively washed with water and the wet cells are collected. By drying these cells, dry bacterial cells are obtained. Drying of the cells may be carried out by freeze-drying, air-drying and such. Such wet or dry cells comprise DPA-containing lipids, and these cells may be used directly for the purpose of this invention. Preferably, DPA-containing lipids are extracted by further extraction of the dried cells under a stream of nitrogen using organic solvents. Ether, hexane, methanol, ethanol, chloroform, dichloromethane, petroleum ether and such may be used as organic solvents. Alternative extraction with methanol and petroleum ether, and extraction using a monophasic solvent consisting of chloroform-methanol-water can also yield good results. Removal of organic solvent from the extract under reduced pressure yields DPA-containing lipid extract, which may be used for the purpose of this invention.

Various highly unsaturated fatty acids are included as components of lipid within the lipid extract obtained as described above. It is possible to separate the lipids according to different types by directly subjecting the lipid extract to the appropriate purification steps (for example, chromatography). More preferably, purification is carried out after conversion of the highly unsaturated fatty acids in the lipid extract to the esters of lower alcohols (for example, DPA ethyl ester, DHA ethyl ester, EPA ethyl ester, and so on). Such esterification will facilitate the separation of DPA ester as a DPA-containing lipid from lipid components that do not contain DPA. This will also facilitate the separation of other fatty acids such as palmitic acid, oleic acid, and such (these are also esterified during the esterification of highly unsaturated fatty acids) that may be produced during cultivation of the microorganisms.

Esterification of highly unsaturated fatty acids can be carried out using known conditions. For example, to obtain the ethyl ester, the extracted lipids mentioned above is preferably treated by reagents such as 5~10% HCl-anhydrous ethanol solution, 10~50% $BF_3$-ethanol solution, and such for 1~24 hours at room temperature.

To collect the highly unsaturated fatty acid ethyl ester from the above-mentioned solution, extraction by organic solvents such as hexane, ether, and ethyl acetate is preferred. Upon drying this extract over drying agents such as sodium sulfate, the organic solvent is removed, preferably under reduced pressure, to yield a mixture containing fatty acid esters as its major component. This mixture also contains a variety of fatty acid ethyl esters besides DPA ethyl ester. This mixture may be used for the purpose of this invention. If necessary, column chromatography, low temperature crystallization, urea addition, liquid-liquid counter current distribution chromatography, and such may be used alone or in combination to isolate the DPA ethyl ester from the mixture. The obtained purified DPA ethyl ester may be used especially favorably for the purpose of this invention.

In order to obtain free DPA from the purified DPA ethyl ester, which is isolated as described above, the ester should be hydrolyzed by alkali then extracted with organic solvents such as ether, ethyl acetate and such. The obtained free DPA and its salt may be used for the purpose of this invention. To prepare free DPA not via its esterified derivative, the lipid extract mentioned above is subjected to alkaline hydrolysis under appropriate conditions (for example, under 5% sodium hydroxide at room temperature for 2~3 hours). From the hydrolysis reaction solution, free DPA can be obtained by extraction of fatty acids following standard purification methods.

(Novel Lipids Containing DPA)

This invention introduces novel lipids that may be utilized favorably as DPA-containing lipids. These lipids contain ARA, DPA, and DHA (and optionally EPA), and are characterized by the combination of three ratios, ARA/DHA, DPA/DHA, and EPA/DHA (each expressed by their weight ratio). Typically the ARA/DHA ratio is 0.03~0.4, preferably 0.05~0.4, and more preferably 0.1~0.4. Typically the DPA/DHA ratio is not less than 0.07, preferably 0.07~5.0, more preferably 0.07~3.0, and evenmore preferably 0.07~0.5. The EPA/DHA ratio is typically not more than 0. 05, preferably not more than 0.04%, and more preferably not more than 0.03%. In general, when the three ratios are within this range, the amount of DPA may be effective for preventing decrease of ARA levels caused by the intake of ω3 unsaturated fatty acids (that is, DHA, and when present, EPA).

The lipids mentioned above are preferably lipids that are obtained by cultivating one type of microorganism (that is, lipids derived from microbial cells obtained by cultivating one or more batches of a certain microorganism), or a mixture of lipids obtained by separately cultivating many different microorganisms (that is, lipid derived from microbial cells obtained by separately cultivating one or multiple batches of two or more different microorganisms). The lipids of this invention may be obtained by combining lipids that are obtainable by cultivating microorganisms that can produce DPA and DHA while hardly producing any EPA such as the genus Thraustochytrium, genus Schizochytrium, genus Japonochytrium, and genus Ulkenia, with lipids obtainable by cultivating microorganisms that can produce ARA but hardly produces any EPA, such as the species alpina, banieri, elongate, exigua, minutissima, verticilata, hygrophila, polycephla, and schmuckeri belonging to the sub genus Mortierella of the genus Mortierella. In this lipid, each of ARA, DPA, and DHA (and optionally EPA) may exist within the glycerol ester and may exist especially in triglycerides.

The novel lipids mentioned above relieve ARA deficient conditions and maintain a good fatty acid balance in vivo, or show the effect of preventing decrease of ARA levels. At the same time, they are useful because they contain a relatively small amount of ARA themselves, the naturally strong physiological effect of ARA towards the body is hardly seen, and their effect on the body is mild. Accordingly, this lipid may be utilized favorably as a component of nutrient-supplementing foods including formula for feeding infants, formula for premature infants, baby foods, foods for expectant and nursing mothers, geriatric foods, and foods for sick patients where enrichment of ARA and DHA is desired, and as feeds for animals.

EXAMPLES

Hereinafter, the present invention will be specifically described by way of examples. However, the invention is not limited to these examples.

Example 1

Method for Producing DPA-containing Lipids and DPA Ethyl Ester using Microorganisms Having the Ability to Produce DPA The SAM2179 strain of the genus Ulkenia was cultivated under the following conditions in a 200 L fermenter (jar fermenter type) containing 120 L of medium having the following composition.

| (1) Medium composition | |
|---|---|
| 1) Glucose (g/L): | 60 |
| 2) Potassium phosphate (g/L): | 3 |
| 3) Ammonium sulfate (g/L): | 2 |
| 4) Magnesium chloride (g/L): | 1.3 |
| 5) Sodium sulfate (g/L): | 1 |
| 6) Calcium chloride (g/L): | 0.3 |
| 7) Corn steep liquor (g/L): | 0.7 |
| 8) pH: | 4.0 |
| (2) Culture condition | |
| 1) Culturing temperature (° C.): | 28 |
| 2) Airation amount (vvm): | 0.5 |
| 3) Agitation rate (rpm): | 300 |
| 4) pH Adjustment: maintained at pH 4 with 10% (w/v) sodium hydroxide and 1 M sulfuric acid | |

After cultivation, the cells were collected by centrifugation and freeze-dried to prepare driedcells. As a result, 2.4 kg of dried cells containing 58% of lipid that contains 12.1% of DPA with respect to the total amount of fatty acid in the lipid were collected.

Next, from 2 kg of the obtained dried cells, DPA-containing lipids were extracted with hexane. Upon removal of solvent, the extracted oil was purified to a grade suitable for foods through food oil purification steps, deodorization, deacidification, degumming, and decoloration, to yield 815 g of purified oil containing 12.8% of DPA with respect to the total amount of fatty acids in the purified oil. Furthermore, a portion of the purified oil was converted to ethyl esters and purification to high purity was performed by high-speed liquid chromatography to yield 10 g of 99% DPA ethyl ester.

Example 2

Demonstration of Decrease in ARA Levels Caused by DHA Intake

Four-week-old male Wistar rats were initially raised for one week, and then divided into 2 groups described below.
1) Control group
  perilla oil: safflower oil=7:3
2) DHA group
  rapeseed oil: DHA ethyl ester=3:2

For 4 weeks, the rats were fed experimental diets prepared by mixing 5% of the indicated oils for each of the groups to the basal feed. Table 1 shows the fatty acid composition of the oils added to each of the groups.

TABLE 1

Fatty acid composition of the oils added to each of the groups (%)

| | 16:0 | 18:0 | 18:1 (n-9) | 18:2 (n-6) | 18:3 (n-3) | DPA (n-6) | DHA (n-3) |
|---|---|---|---|---|---|---|---|
| control group | 6.7 | 2.1 | 36.7 | 14.1 | 40.3 | — | — |
| DHA group | 2.4 | 1.0 | 35.2 | 13.1 | 6.5 | — | 40.0 |

16:0, palmitic acid; 18:0, stearic acid; 18:1 (n-9), oleic acid; 18:2 (n-6), linoleic acid; 18:3 (n-3), α-linolenic acid The livers were excised from the raised rats of both groups, and lipids were extracted by the Folch method and upon conversion to the methyl ester, the amount of each fatty acid was analyzed by gas chromatography. The fatty acid composition in the livers of each group is shown in Table 2.

TABLE 2

Fatty acid composition in the livers of each group (%)

| | control group | DHA group |
|---|---|---|
| 18:0 | 28.7 ± 3.41 | 22.6 ± 1.27‡‡‡ |
| 18:1 (n-9) | 22.9 ± 5.80 | 23.0 ± 2.49 |
| 18:2 (n-6) | 25.1 ± 4.29 | 13.3 ± 1.96‡‡‡ |
| 18:3 (n-3) | 8.83 ± 1.75 | 1.03 ± 0.21‡‡‡ |
| 20:3 (n-6) | 1.03 ± 0.35 | 0.78 ± 0.15 |
| 20:4 (n-6) | 24.1 ± 2.75 | 6.18 ± 0.79‡‡‡ |
| 20:5 (n-3) | 5.26 ± 1.20 | 10.5 ± 1.57‡‡‡ |
| 22:5 (n-6) | — | — |
| 22:5 (n-3) | 2.98 ± 0.20 | 1.49 ± 0.35‡‡‡ |
| 22:6 (n-3) | 9.59 ± 0.83 | 24.7 ± 2.23‡‡‡ |

The values are shown as: mean±standard deviation

18:0, stearic acid: 18:1 (n-9), oleic acid; 18:2 (n-6), linoleic acid; 18:3 (n-3), α-linolenic acid; 20:3 (n-6), dihomo-γ-linolenic acid; 20:4 (n-6), arachidonic acid: 20:5 (n-3), 5, 8, 11, 14, 17-eicosapentaenoic acid: 22:5 (n-6), 4, 7, 10, 13, 16-docosapentaenoic acid: 22:5 (n-3), 7, 10, 13, 16, 19-docosapentaenoic acid: 22:6 (n-3), 4, 7, 10, 13, 16, 19-docosahexaenoic acid Presence of significant difference compared to the control value, P<0.001

The control group and DHA group both contain similar amounts of linoleic acid, which is the precursor of ARA. Upon administration of DHA, significant decrease in the proportion of ARA is confirmed. Furthermore, although the fraction of ω3 unsaturated fatty acids present in the added lipids of the control group and the DHA group are 40.3% and 46.5%, respectively, and is hardly different, significant decrease of ARA levels due to DHA addition was indicated.

Example 3

The Effect of Preventing Decrease of ARA Levels, Which is Caused by DHA Intake, Through DPA Intake (1)

Four-week-old male Wistar rats were initially raised for one week, and then divided into two groups described below.
1) control group
  soybean oil
2) DPA group
  purified oil obtained in Example 1: olive oil=4:1

For 4 weeks, the rats were fed experimental diets prepared by mixing 5% of the indicated oils for each of the groups to the basal feed. The fatty acid compositions of the oil added to each group are shown in Table 3.

TABLE 3

Fatty acid composition of oils added to each group (%)

| | 16:0 | 18:0 | 18:1 (n-9) | 18:2 (n-6) | 18:3 (n-3) | DPA (n-6) | DHA (n-3) |
|---|---|---|---|---|---|---|---|
| control group | 14.1 | 5.1 | 2.9 | 68.1 | 9.9 | — | — |
| DPA group | 32.5 | 2.0 | 17.2 | 2.8 | 0.2 | 10.3 | 34.9 |

16:0, palmitic acid; 18:0, stearic acid; 18:1 (n-9), oleic acid; 18:2 (n-6), linoleic acid; 18:3 (n-3), (α-linolenic acid The livers were excised from the raised rats from each group, and lipids were extracted by the Folch method and upon conversion to the methyl ester, the amount of each fatty acid was analyzed by gas chromatography. The fatty acid compositions in the livers of each group are indicated in Table 4.

TABLE 4

Fatty acid composition in the livers of each group (%)

| | control group | DHA group |
|---|---|---|
| 16:0 | 37.9 ± 5.57 | 34.0 ± 2.66 |
| 18:0 | 25.1 ± 1.54 | 23.2 ± 1.12 |
| 18:1 (n-9) | 28.9 ± 3.97 | 19.3 ± 3.47 |
| 18:2 (n-6) | 30.1 ± 4.20 | 4.14 ± 0.50 |
| 18:3 (n-3) | 1.56 ± 0.40 | 0.04 ± 0.06‡‡‡ |
| 20:4 (n-6) | 29.9 ± 2.15 | 22.4 ± 1.60‡‡‡ |
| 20:5 (n-3) | — | 3.94 ± 0.89‡‡‡ |
| 22:5 (n-6) | — | 4.30 ± 0.76 |
| 22:6 (n-3) | 8.32 ± 1.63 | 30.5 ± 4.28‡‡‡ |

The values are shown as: mean±standard deviation

16:0, palmitic acid; 18:0 stearic acid; 18:1 (n-9), oleic acid; 18:2 (n-6), linoleic acid; 18:3 (n-3), α-linolenic acid; 20:4 (n-6), arachidonic acid; 20:5 (n-3), 5, 8, 11, 14, 17-eicosapentaenoic acid; 22:5 (n-6), 4, 7, 10, 13, 16-docosapentaenoic acid; 22:6 (n-3), 4, 7, 10, 13, 16, 19-docosahexaenoic acid

*** Presence of significant difference compared to the control value, P<0.001

The control group (soybean oil) of this example has a ratio of ω3 unsaturated fatty acids to 0)6 unsaturated fatty acids that is close to the ratio of intake under normal living conditions. Compared to the DHA group of Example 2, the DPA group of this example was capable of preventing ARA decrease, even though the DHA content was 34.9%. That is, although somewhat lower, an ARA value close to that of the control group of this example was indicated. This effect was clearly observed even when the amount of DPA was less than the absolute amount of DHA.

Example 4
The Effect of Preventing Decrease of ARA Levels, Which is Caused by DHA Intake, Through DPA Intake (2)

Four-week-old male Wistar rats were initially raised for one week, and then divided into 4 groups described below.

1) linoleic acid 15-DPA 10 group (LA15DPA10)
   purified oil obtained in Example 1: safflower oil=4:1
2) linoleic acid 10-arachidnoic acid 5-DPA 10 group (LA10AA5DPA10)
   rapeseed oil: arachidonic acid ethyl ester: purified oil obtained in Example 1=15:5:80
3) linoleic acid 15 group (LA15)
   rapeseed oil: DHA ethyl ester=65:35
4) linoleic acid 25 group (LA25)
   (rapeseed oil: soybean oil=1:1): DHA ethyl ester=65:35

For 4 weeks, the rats were fed experimental diets prepared by mixing 5% of the indicated oils for each of the groups to the basal feed. The fatty acid compositions of oils added to each of the groups are shown in Table 5. The amount of DHA was kept nearly constant (30–35%) while ω6 type linoleic acid, ARA, and DPA were varied.

TABLE 5

Fatty acid composition of these added oils in each of the groups (%)

| | 16:0 | 18:0 | 18:1 (n-9) | 18:2 (n-6) | 18:3 (n-3) | 20:4 (n-6) | DPA (n-6) | DHA (n-3) |
|---|---|---|---|---|---|---|---|---|
| group 1 | 31.41 | 1.95 | 3.85 | 16.88 | — | — | 10.19 | 35.72 |
| group 2 | 33.66 | 1.65 | 2.42 | 11.18 | — | 5.06 | 10.19 | 35.54 |
| group 3 | 3.76 | 1.83 | 42.11 | 15.95 | 5.88 | — | — | 30.47 |
| group 4 | 5.49 | 2.39 | 29.0 | 26.4 | 6.00 | — | — | 30.72 |

16:0 palmitic acid; 18:0 stearic acid; 18:1 (n-9) oleic acid; 18:2 (n-6), linoleic acid; 18:3 (n-3), α-linolenic acid; 20:4 (n-6), arachidonic acid The blood and livers were obtained from the raised rats of each of the groups and lipids were extracted by the Folch method and upon conversion to the methyl ester, the amount of each fatty acid was analyzed by gas chromatography. Table 6 shows the fatty acid compositions in the livers from each of the groups.

TABLE 6

Fatty acid composition in the livers from each group (μmol/g)

| | LA15DPA10 | LA10AA5DPA10 | LA15 | LA25 |
|---|---|---|---|---|
| 18:0 | 25.0 ± 2.15 | 24.2 ± 4.18 | 24.1 ± 1.37 | 24.8 ± 1.19 |
| 18:1 (n-9) | 16.2 ± 2.64 | 23.7 ± 3.63 | 18.8 ± 2.65 | 20.7 ± 6.08 |
| 18:2 (n-6) | 13.0 ± 1.75 a | 11.0 ± 3.44 a | 13.5 ± 2.02 a | 20.2 ± 1.74 b |
| 18:3 (n-3) | 0.05 ± 0.11 a | 0.20 ± 0.06 a | 0.99 ± 0.44 b | 1.19 ± 0.17 b |
| 20:4 (n-6) | 20.8 ± 1.84 a | 29.9 ± 3.73 b | 8.00 ± 0.82 c | 8.60 ± 1.36 c |
| 20:5 (n-3) | 2.16 ± 0.62 a | 1.97 ± 0.70 a | 6.05 ± 1.54 b | 4.27 ± 0.64 c |
| 22:5 (n-6) | 6.94 ± 1.95 | 8.31 ± 2.51 | — | |
| 22:6 (n-3) | 44.9 ± 8.38 ab | 55.0 ± 10.9 a | 32.1 ± 5.94 b | 43.9 ± 7.68 ab |

The values are shown as: mean±standard deviation

18:0 stearic acid; 18:1 (n-9), oleic acid; 18:2 (n-6), linoleic acid; 18:3 (n-3), α-linolenic acid; 20:4 (n-6), arachidonic acid; 20:5 (n-3), 5, 8, 11, 14, 17-eicosapentaenoic acid; 22:5 (n-6), 4, 7, 10, 13, 16-docosapentaenoic acid: 22:6 (n-B), 4, 7, 10, 13, 16, 19-docosahexaenoic acid Presence of significant difference among the values are indicated by different letters, a, b, and c; P<0.05 from each group.

Table 7 indicates the fatty acid compositions in serum

TABLE 7

Fatty acid composition in the sera from each group ($\mu$mol/g)

| | LA15DPA10 | LA10AA5DPA10 | LA15 | LA25 |
|---|---|---|---|---|
| 18:0 | 0.78 ± 0.13 a | 0.57 ± 0.12 b | 0.83 ± 0.05 a | 0.76 ± 0.09 ab |
| 18:1 (n-9) | 0.68 ± 0.16 a | 0.53 ± 0.18 a | 1.36 ± 0.07 b | 1.16 ± 0.99 b |
| 18:2 (n-6) | 0.50 ± 0.11 a | 0.26 ± 0.11 b | 0.89 ± 0.05 c | 0.99 ± 0.12 c |
| 18:3 (n-3) | — | — | 0.05 ± 0.01 | 0.04 ± 0.01 |
| 20:4 (n-6) | 1.68 ± 0.53 a | 1.30 ± 0.27 a | 0.51 ± 0.04 b | 0.50 ± 0.09 b |
| 20:5 (n-3) | 0.12 ± 0.07 ab | 0.05 ± 0.04 a | 0.37 ± 0.01 b | 0.26 ± 0.13 b |
| 22:5 (n-6) | 0.14 ± 0.05 | 0.11 ± 0.05 | — | |
| 22:6 (n-3) | 0.90 ± 0.25 ab | 0.63 ± 0.22 a | 1.14 ± 0.35 b | 1.16 ± 0.14 b |

The values are shown as: average value±standard deviation

18:0 stearic acid; 18:1 (n-9), oleic acid; 18:2 (n-6), linoleic acid; 18:3 (n-3), α-linolenic acid: 20:4 (n-6), arachidonic acid; 20:5 (n-3), 5, 8, 11, 14, 17-eicosapentaenoic acid; 22:5 (n-6), 4, 7, 10, 13, 16-docosapentaenoic acid; 22:6 (n-3), 4, 7, 10, 13, 16, 19-docosahexaenoic acid Presence of significant difference among the values are indicated by different letters, a, b, and c; $P<0.05$ The results on fatty acid composition within the liver, described in Table 6, show that ARA levels decreased significantly in group 3 (LA15) and group 4 (LA25), which were not supplied with DPA, compared to group 1 (LA15DPA10) and group 2 (LA10AA5DPA10), which were supplied with DPA. Even when a large supply of linoleic acid, which is the precursor of ARA, was given (to group 4), decrease of ARA levels due to intake of DHA could not be repressed sufficiently. The fatty acid composition in serum, shown in Table 7, was similar to the fatty acid composition results obtained for the liver.

Example 5
Preparation of DPA Containing Capsules

Water was added to 100 part gelatin and 35 part food additive glycerol by weight, and after dissolution at 50–60° C., Gelatin film with viscosity of 20,000 cps was prepared. Next, 97% of the purified oil obtained in Example 1 and 3% of vitamin E oil were mixed to prepare the contents. Using these materials, capsule formation and drying were carried out by standard procedures to produce soft capsules containing 180 mg of content per capsule.

Example 6
Preparation of a Fat and Oil Mixture Containing DPA, DHA, and ARA

A fat and oil mixture was prepared by mixing the purified oil containing DPA, obtained in Example 1 with purified oil containing ARA, which was purified by standard procedures from a *Mortiella alpina* culture (4:1). Table 8 shows the fatty acid composition of the obtained fat and oil mixture.

Example 7
Preparation of Capsules Containing DPA, DHA, and ARA

A gelatin membrane was prepared using the same method as in Example 5. Next, the content was prepared by mixing 97% of the fat and oil mixture obtained in Example 7 and 3% of vitamin E. Capsule formation using these materials and drying carried out by standard methods yielded soft capsules containing 180 mg of content per capsule.

INDUSTRIAL APPLICABILITY

Use of DPA-containing material and compositions containing DPA-containing materials of this invention enables relief of ARA deficient conditions and maintenance of a good fatty acid balance In viva, and prevention of decrease of ARA levels caused by intake of a ω3 unsaturated fatty acids. DPA is converted to ARA in vivo, and in contrast to ARA, it is not the direct precursor of eicosanoids. Therefore, this-may substitute direct administration of ARA and provide a technique that has milder influence on the body.

What is claimed is:

1. A method for relieving arachidonic acid deficient conditions and maintaining a good fatty acid balance in vivo in mammals excluding humans, comprising the process of administering 4, 7, 10, 13, 16-docosapentaenoic acid (DPA)-containing material in an amount efficacious in increasing said arachidonic acid levels per unit dose.

2. A method for the production of composition that prevents the decrease of arachidonic acid levels caused by intake of ω3 unsaturated fatty acids, comprising; determining the average intake of ω3 unsaturated fatty acids during a set period of time in a subject; estimating the decrease of arachidonic acid levels brought forth by intake of said ω3 unsaturated fatty acids to the subject; and preparing a unit dose of said composition containing DPA-containing material in an amount effective for preventing decrease of said arachidonic acid levels.

3. A method for the production of composition that prevents the decrease of arachidonic acid levels caused by intake of ω3 unsaturated fatty acids, comprising: determining the amount of ω3 unsaturated fatty acids to be included per unit dose in said composition; estimating the decrease of

TABLE 8

Fatty acid composition of the fat and oil mixture containing DPA, DHA, and ARA (%)

| 16:0 | 18:0 | 18:1 (n-9) | 18:2 (n-6) | 18:3 (n-6) | 20:3 (n-6) | ARA | EPA | DPA | DHA | 22:0 | 24:0 | residual |
|---|---|---|---|---|---|---|---|---|---|---|---|---|
| 30.1 | 2.3 | 1.5 | 2.3 | 0.5 | 0.8 | 8.1 | 0.1 | 10.2 | 36.6 | 0.5 | 1.0 | 6 | arachidonic acid levels caused by intake of said ω3 unsaturated fatty acids in a subject; and preparing a unit dose of said composition containing DPA-containing material and ω3 unsaturated fatty acid-containing material in amounts effective for preventing decrease of said arachidonic acid levels.

4. The methods according to claim 3, wherein said DPA-containing material and ω3 unsaturated fatty acid-containing material are lipids containing DPA and ω3 unsaturated fatty acids, and the amount of DPA with respect to the total amount of fatty acids in said composition is not less than 0.1%.

5. The methods according to claim 3, wherein said DPA-containing material and ω3 unsaturated fatty acid-containing material are lipids containing DPA and ω3 unsaturated fatty acids and the amount of DPA with respect to the total amount of fatty acids within said composition is not less than 0.1%, and the amount of 4, 7, 10, 13, 16, 19-docosahexaenoic acid (DHA) is not less than 0.1%.

6. The method according to claim 3, wherein said DPA-containing material and ω3 unsaturated fatty acid-containing material are lipids containing DPA and ω3 unsaturated fatty acids, and with respect to the total amount of fatty acids within said composition, the amount of DPA is not less than 0.1%, DHA is not less than 0.1%, and 5, 8, 11, 14, 17-eicosapentaenoic acid (EPA) is not more than 20%.

7. The method according to claim 4, wherein said lipids containing DPA and (ω3) type unsaturated fatty acids comprise any one or more of the compounds selected from a group consisting of lower alkyl esters of DPA, lower alkyl esters of (ω3) type unsaturated fatty acids, and glycerol esters containing DPA and/or (ω3) type unsaturated fatty acids as components.

8. A lipid containing arachidonic acid (ARA), DPA, and DHA, in which ARA/DHA (weight ratio) is 0.03~0.4, DPA/DHA (weight ratio) is not less than 0.07, and EPA/ DHA (weight ratio) is not more than 0.05.

9. The lipid according to claim 8, wherein said DPA/DHA (weight ratio) is 0.07~5.0.

10. The lipid according to any one of claims 8 or 9, wherein said lipid is obtained by cultivating one type of microorganism, or a mixture of lipids obtained by separately cultivating different types of microorganisms.

11. The lipid according to claim 8, wherein said lipid includes glycerol esters containing ARA, DPA and/or DHA as components.

12. The lipid according to claim 8, wherein said lipid includes triglycerides containing ARA, DPA and/or DHA as components.

13. A nutrient-supplementing food comprising the lipid according to claim 8.

14. The nutrient-supplementing food according to claim 13, which is formula for feeding infants, formula for premature infants, baby food, food for expectant and nursing mothers, geriatric food, or food for adults.

15. A feed for animals comprising the lipid according to claim 8.

16. The method according to claim 1, wherein said DPA-containing material is one or more of DPA-containing lipids selected from a group consisting of lower alkyl esters of DPA and DPA containing glycerol esters.

17. A method for relieving arachidonic acid deficient conditions and maintaining a good fatty acid balance in vivo in humans, comprising the process of administering 4, 7, 10, 13, 16-docosapentaenoic acid (DPA)-containing material in an amount efficacious in increasing said arachidonic acid levels per unit dose.

18. The method according to claim 17, wherein said DPA-containing material is one or more of DPA-containing lipids selected from a group consisting of lower alkyl esters of DPA and DPA containing glycerol esters.

19. A method for preventing the decrease of arachidonic acid levels caused by intake of (ω3) type unsaturated fatty acids, comprising the process of administering 4, 7, 10, 13, 16-docosapentaenoic acid (DPA)-containing material in an amount effective for preventing the decrease of said arachidonic acid levels per unit dose.

20. The method according to claim 19, where the DPA-containing material is one or more of DPA containing lipids selected from a group consisting of lower alkyl esters of DPA and DPA-containing glycerol esters.

21. The method according to claim 20, wherein said DPA-containing lipids are obtained from microorganisms.

22. The method according to claim 21, wherein said microorganisms are selected from a group consisting of the genus Thraustochytrium, genus Schizochytrium, genus Japonochytrium, and genus Ulkenia.

23. A nutrient-supplementing food comprising the lipid according to claim 9.

24. A nutrient-supplementing food comprising the lipid according to claim 10.

25. A nutrient-supplementing food comprising the lipid according to claim 11.

26. A nutrient-supplementing food comprising the lipid according to claim 12.

27. The nutrient-supplementing food according to claim 9, which is formula for feeding infants, formula for premature infants, baby food, food for expectant and nursing mothers, geriatric food, or food for adults.

28. The nutrient-supplementing food according to claim 10, which is formula for feeding infants, formula for premature infants, baby food, food for expectant and nursing mothers, geriatric food, or food for adults.

29. The nutrient-supplementing food according to claim 11, which is formula for feeding infants, formula for premature infants, baby food, food for expectant and nursing mothers, geriatric food, or food for adults.

30. The nutrient-supplementing food according to claim 12, which is formula for feeding infants, formula for premature infants, baby food, food for expectant and nursing mothers, geriatric food, or food for adults.

31. The nutrient-supplementing food according to claim 23, which is formula for feeding infants, formula for premature infants, baby food, food for expectant and nursing mothers, geriatric food, or food for adults.

32. The nutrient-supplementing food according to claim 24, which is formula for feeding infants, formula for premature infants, baby food, food for expectant and nursing mothers, geriatric food, or food for adults.

33. The nutrient-supplementing food according to claim 17, fit which is formula for feeding infants, formula for premature infants, baby food, food for expectant and nursing mothers, geriatric food, or food for adults.

34. The nutrient-supplementing food according to claim 26, which is formula for feeding infants, formula for premature infants, baby food, food for expectant and nursing mothers, geriatric food, or food for adults.

* * * * *